United States Patent [19]

Chaumette et al.

[11] Patent Number: 5,783,607
[45] Date of Patent: Jul. 21, 1998

[54] PROCESS FOR CONVERTING SYNTHESIS GAS IN THE PRESENCE OF A CATALYST BASED ON COBALT AND TITANIUM

[75] Inventors: Patrick Chaumette, Bougival; Olivier Clause, Chatou; Hedi Azib, L'Hay les Roses, all of France

[73] Assignees: Institut Francais du Petrole, Cedex, France; AGIP Petroli S.p.A., Rome, Italy

[21] Appl. No.: 835,523

[22] Filed: Apr. 8, 1997

[30] Foreign Application Priority Data

Apr. 9, 1996 [FR] France ................. 96 04417

[51] Int. Cl.$^6$ ................. C07C 27/00; C07C 1/00; B01J 23/00
[52] U.S. Cl. ................. 518/713; 518/715; 518/722; 502/302; 502/327; 502/328; 502/329; 502/331; 502/332; 502/333; 502/334; 502/350; 502/345; 585/700; 585/733
[58] Field of Search ................. 518/713, 715, 518/717, 722; 585/700, 733; 502/302, 327, 328, 329, 331, 332, 333, 334, 350, 345

[56] References Cited

U.S. PATENT DOCUMENTS 4,176,089  11/1979  Cull ................. 252/452
5,169,821  12/1992  Soled et al. ................. 502/242

FOREIGN PATENT DOCUMENTS 0 398 420  11/1990  European Pat. Off. .
0 455 308  11/1991  European Pat. Off. .
0 629 442  12/1994  European Pat. Off. .

*Primary Examiner*—Glenn Caldarola
*Assistant Examiner*—In Suk Bullock
*Attorney, Agent, or Firm*—Millen, White, Zelano & Branigan, P.C.

[57] ABSTRACT

The invention concerns the preparation of a catalyst comprising a support comprising at least one oxide of the element Si, Al, Ti, Zr, Sn, Zn, Mg or Ln (where Ln is a rare earth), cobalt, titanium, at least one element A selected from the group formed by copper, ruthenium, platinum, palladium, scandium and yttrium, and characterized in that it comprises at least the following successive steps:

(1) forming a precursor comprising at least cobalt, element A and the support;
(2) at least partial reduction of said precursor in the presence of at least one reducing compound; and
(3) depositing titanium on the reduced precursor.

The invention also concerns the catalyst which can be produced using this process and the use of the catalyst in a process for synthesizing $C_5^+$ hydrocarbons from synthesis gas.

9 Claims, No Drawings

PROCESS FOR CONVERTING SYNTHESIS GAS IN THE PRESENCE OF A CATALYST BASED ON COBALT AND TITANIUM

The present invention concerns a catalytic formulation, its preparation and its use in a process for synthesizing hydrocarbons from a CO—($CO_2$)—$H_2$ mixture, i.e., a CO—$H_2$ mixture which may contain $CO_2$, known as synthesis gas, more particularly the use thereof to convert synthesis gas to a mixture of linear and saturated hydrocarbons essentially constituted by $C_5^+$ hydrocarbons (i.e., containing at least 5 carbon atoms per molecule), or more precisely to a mixture of essentially linear and saturated hydrocarbons containing at least 25% by weight of $C_5^+$ hydrocarbons with respect to the total of the hydrocarbons formed.

Synthesis gas is known to be converted to hydrocarbons in the presence of catalysts containing transition metals. This conversion, operated at high temperatures and under pressure, is known as the Fischer-Tropsch synthesis. Metals from group VIII of the periodic classification of the elements such as iron, ruthenium, cobalt and nickel catalyse the transformation of CO—($CO_2$)—$H_2$ mixtures to liquid and/or gaseous hydrocarbons.

The products prepared by the Fischer-Tropsch process in the presence of catalysts comprising group VIII metals have a very wide molecular weight distribution. Thus only a small proportion of the products obtained are situated in the range of middle distillates constituted by kerosine and gas oil fractions, the kerosine fraction(s) being constituted by a mixture of hydrocarbons with boiling points which are in the range 140° C. to 300° C., and the gas oil fractions being constituted by a mixture of hydrocarbons with boiling points which are in the range 180° C. to 370° C. during atmospheric distillation as would be carried out by the skilled person on crude oil.

Since 1973, great efforts have been made to improve the yield of middle distillates from processes based on synthesis gas conversion. Thus the catalyst described in U.S. Pat. No. 5,302,622, comprising cobalt, copper and ruthenium and prepared by gelation, produces a mixture of essentially linear and saturated hydrocarbons containing at least 80% by weight of $C_5^+$ hydrocarbons with respect to the total amount of hydrocarbons formed.

These formulations can synthesise essentially paraffinic, linear hydrocarbons. However, a substantial proportion of these hydrocarbons is constituted by paraffins with high boiling points, i.e., with boiling points which are above that of middle distillates.

Such high boiling point hydrocarbons are thus advantageously treated in a hydrocracking process which is normally used for treating heavy cuts from a crude oil, in order to improve the yield of middle distillates.

In some cases, however, it is advantageous to synthesise a mixture of essentially linear saturated hydrocarbons generally containing less than 80% of $C_5^+$ hydrocarbons, and preferably 25% to 70% by weight of $C_5^+$ hydrocarbons. Such a mixture contains a high proportion of hydrocarbons which are liquid at ambient temperature and at atmospheric pressure.

After simple fractionation (for example atmospheric distillation), such an essentially liquid product constitutes a synthetic crude which can readily be transported and/or mixed with a crude oil then processed separately or as a mixture in conventional refinery units.

U.S. Pat. No. 4,522,939 describes a process for the preparation of a Fischer-Tropsch catalyst based on cobalt and containing a second metal selected from zirconium, titanium or chromium and supported on silica, alumina or silica-alumina. That catalyst is prepared by impregnation or mixing and the second metal is introduced before, after or simultaneously with introduction of the cobalt. Preferably, the catalyst is calcined after each introduction. Reduction after the various impregnation or mixing steps leading to the production of the catalyst is not anticipated, a single reduction step being carried out after preparation of the catalyst and before the catalytic test. Such catalysts deactivate to a greater or lesser extent over time.

Patents U.S. Pat. No. 4,794,099 and U.S. Pat. No. 4,960,801 describe catalysts based on cobalt and optionally rhenium deposited on supports based on titanium oxide. In U.S. Pat. No. 4,794,099, a silicon based precursor is added to the titanium oxide before or after deposition of cobalt and rhenium, to improve the activity of the catalyst. In U.S. Pat. No. 4,960,801, an aluminium, zirconium, or silicon based binder is added to the titanium oxide based support to increase the porosity of the support. Similarly, a single reduction step is provided after calcining the catalyst containing all of the elements and before the catalytic test.

SUMMARY OF THE INVENTION

The present invention describes the preparation of a Fischer-Tropsch catalyst with performances which are particularly stable, and which after reduction in hydrogen leads to the conversion of synthesis gas to a mixture of essentially linear and saturated hydrocarbons containing at least 25% by weight of $C_5^+$ hydrocarbons with respect to the total amount of hydrocarbons formed.

The present invention provides a process for the preparation of a catalyst comprising a support selected from the group formed by at least one oxide of an element selected from the group formed by the following elements: Si, Al, Ti, Zr, Sn, Zn, Mg or Ln (where Ln is a rare earth, i.e., an element with an atomic number which is between 57 and 71 inclusive), preferably selected from the group formed by silica, alumina, zirconia and titanium oxide, cobalt, titanium, at least one additional element A selected from the group formed by copper, ruthenium, platinum, palladium, scandium and yttrium, the process being characterized in that the catalyst preparation comprises at least the following successive steps:

(1) forming a precursor comprising at least cobalt, element A and the support;

(2) at least partial reduction of said precursor in the presence of at least one reducing compound; and (3) depositing titanium on the reduced precursor.

The catalyst prepared in accordance with the invention generally comprises, in % by weight of the element with respect to the weight of the support in the catalyst, between 1% and 60%, preferably between 2% and 50%, of cobalt, between 0.01% and 20%, preferably between 0.05% and 10%, of additional element A and between 0.01% and 15%, preferably between 0.05% and 5%, of titanium.

The invention also concerns the catalyst obtained by the preparation process of the invention, also the use of the catalyst in a process for the synthesis of essentially linear and saturated hydrocarbons containing at least 25% by weight of $C_5^+$ hydrocarbons with respect to the total amount of hydrocarbons formed, from a feed comprising carbon monoxide CO, hydrogen and optionally, carbon dioxide $CO_2$, said feed being known as synthesis gas. The catalyst of the invention has improved stability over prior art catalysts.

Any titanium based compound can be used in the present invention, for example titanium can be incorporated in the form of a halide, oxalate, sulphate, or an alkoxide such as ethyl orthotitanate or isopropyl orthotitanate.

The cobalt and additional element A present in the precursor can be introduced in step (1) using any method which is known to the skilled person, such as ion exchange, dry impregnation, co-precipitation, gelation, ion mixing or grafting of organometallic complexes.

Of these methods, impregnation, co-precipitation, gelation or mixing are preferred for the preparation of said precursor in step (1), as they allow intimate contact between the cobalt and the optional additional element A.

The use of impregnation, co-precipitation, gelation or mixing of cobalt, element A and the support element can generally produce a precursor for a catalyst for the conversion of synthesis gas to hydrocarbons which is active and can lead to the formation of at least 25% by weight of $C_5^+$ hydrocarbons with respect to the total amount of hydrocarbons formed.

A preferred method for the preparation of the catalyst precursor used in accordance with the invention consists, for example, of impregnating the support by means of at least one aqueous solution (or in at least one appropriate solvent) containing cobalt and the additional element A in the form, for example, of a halide, nitrate, acetate, oxalate, sulphate, a complex formed with oxalic acid and oxalates, a complex formed with citric acid and citrates, a complex formed with tartaric acid and tartrates, a complex formed with a further polyacid or alcohol acid and its salts, a complex formed with acetyl acetonates, and any other inorganic or organometallic derivative containing cobalt and additional element A.

After each impregnation of cobalt and additional element A, and optionally the element selected from the group formed by the support elements on the selected support, the precursor obtained is then heat treated, i.e., dried, using any means which is known to the skilled person, for example in a stream of nitrogen or air at a temperature which is in the range 80° C. to 200° C., then calcined, for example in a stream of air or nitrogen at a temperature which is in the range 200° C. to 800° C.

It is also possible to prepare the precursor of the catalyst of the invention using the method described in detail in U.S. Pat. No. 3,975,302 consisting of preparing an impregnating solution from a solid amorphous gel and an alkanolamine, then impregnating a support with that solution.

A further, preferred, method of preparing the precursor of the catalyst of the invention consists of preparing a gel containing cobalt, element A and the support element(s). This gelation preparation can be carried out using any technique which is known to the skilled person. However, a preferred gelation preparation method is described below.

One preferred gelation preparation method consists of preparing a gel obtained by mixing a solution I containing an organometallic compound, preferably an alkoxide of the precursor element(s) of the support, dissolved in an organic solvent, preferably an alcohol, and an aqueous solution II containing a cobalt salt, optionally at least one salt of element A and a support element and also containing an inorganic acid which accelerates gelation, such as nitric acid, hydrochloric acid, sulphuric acid or phosphoric acid. The salts of the cobalt, optional element A and support element(s) are, for example, halides, nitrates, acetates, oxalates, sulphates, complexes formed with a polyacid or acid alcohol and its salts or complexes formed with acetyl acetonates, or any other inorganic derivative which is soluble in an aqueous solution. Mixing solutions I and II with stirring in the presence of said acid produces a gel which is formed in less than 10 minutes and at a temperature which is in the range 20° C. to 80° C. The gel thus formed is separated from the residual solvents using any means which is known to the skilled person, for example centrifuging or filtering, then dried, for example in a stream of nitrogen or air at a temperature which is in the range 80° C. to 200° C., and finally calcined, for example in a stream of air or nitrogen at a temperature which is in the range 200° C. to 800° C.

Step (2) for reducing the precursor formed in step (1) is generally as described below.

The catalyst precursor is first pre-reduced using at least one reducing compound, for example selected from the group formed by hydrogen, carbon monoxide and formic acid, optionally brought into contact with an inert gas (for example nitrogen), in a reducing compound/(reducing compound+inert gas) molar ratio which is in the range 0.001:1 to 1:1.

Reduction is carried out in the gas phase between 150° C. and 600° C., preferably between 200° C. and 500° C., between 0.1 MPa and 10 MNa and at an hourly space velocity which is in the range 100 to 40000 volumes of mixture per volume of catalyst per hour. Reduction can also be carried out in the liquid phase, the catalyst being suspended in an inert solvent, for example a paraffinic cut.

Step (3) for depositing titanium on the reduced precursor is carried out using any technique which is known to the skilled person. A preferred method consists, for example, of impregnating the reduced precursor using at least one aqueous solution I(or in at least one appropriate solvent) containing titanium, for example in the form of a halide, oxalate, sulphate, an alkoxide such as ethyl orthotitanate or isopropyl orthotitanate, a complex formed with oxalic acid and oxalates, a complex formed with citric acid and citrates, a complex formed with tartaric acid and tartrates, a complex formed with a further polyacid or acid alcohol and its salts, a complex formed with acetyl acetonates, and any other inorganic or organometallic derivative containing titanium.

After depositing the titanium, the catalyst obtained is dried, using any means known to the skilled person, for example in a stream of nitrogen or air at a temperature which is in the range 80° C. to 200° C. After drying, the catalyst can optionally be calcined, for example in a stream of air or nitrogen at a temperature which is, for example, in the range 200° C. to 800° C.

The catalyst is optionally formed using any procedure which is known to the skilled person, for example extrusion, oil drop, bowl granulation or pelletizing. After this forming step, the catalyst can optionally be dried using the above operating conditions.

The catalysts prepared using the methods described above are particularly well suited for use in processes for the production of a mixture of essentially linear and saturated hydrocarbons containing at least 25% by weight of $C_5^+$ hydrocarbons, with respect to the total amount of hydrocarbons formed, from a synthesis gas.

The following conditions are used for the production of the hydrocarbons of the invention using said catalysts:

The catalyst, charged into a reactor, is pre-reduced before use using at least one reducing compound, for example selected from the group formed by hydrogen, carbon monoxide and formic acid, optionally brought into contact with an inert gas (for example nitrogen) in a reducing compound/ (reducing compound+inert gas) molar ratio which is in the range 0.001:1 to 1:1.

Pre-reduction is carried out between 150° C. and 600° C., preferably between 200° C. and 500° C., between 0.1 and 10

MPa and at an hourly space velocity which is in the range 100 to 40000 volumes of mixture per volume of catalyst per hour. This pre-reduction can optionally be carried out in a liquid phase comprising at least one hydrocarbon containing at least 5, preferably at least 10, carbon atoms per molecule if, then, the hydrocarbon synthesis reaction is carried out in a liquid phase comprising at least one hydrocarbon containing 5, preferably at least 10, carbon atoms per molecule.

Conversion of synthesis gas to hydrocarbons is then carried out at a total pressure which is normally in the range 0.1 to 15 MPa, preferably in the range 1 to 10 MPa, the temperature generally being in the range 150° C. to 350° C., preferably in the range 170° C. to 300° C.

The hourly space velocity is normally in the range 100 to 20000 volumes of synthesis gas per volume of catalyst per hour, preferably in the range 400 to 5000 volumes of synthesis gas per volume of catalyst per hour, and the $H_2/CO$ ratio in the synthesis gas is normally in the range 1:2 to 5:1, preferably in the range 1.2:1 to 2.5:1.

The catalyst is generally used in the form of a fine calibrated powder (about 10–700 mm) or in particles with an equivalent diameter which is in the range of about 2 to 10 mm, respectively in the presence of a phase which is liquid (under the operating conditions) and a gas phase, or a gas phase. The liquid phase may be constituted by at least one hydrocarbon containing at least 5, preferably at least 10, carbon atoms per molecule.

The catalysts of the invention are particularly active and stable in the reaction which synthesises hydrocarbons from synthesis gas. Finally, said catalysts can produce essentially linear and saturated hydrocarbons containing at least 25% of $C_5^+$ hydrocarbons with respect to the total amount of hydrocarbons formed.

The following examples illustrate the invention.

EXAMPLE 1

(In Accordance with the Invention): Catalyst I

A solution 1 containing 130 g of ethyl orthosilicate (TEOS) dissolved in 50 ml of ethanol and a solution 2 containing 46.3 g of hexahydrated cobalt nitrate, 0.21 g of ruthenium hexamine trichloride and 32 g of concentrated nitric acid dissolved in 80 cm³ of water, were mixed with vigorous stirring at ambient temperature.

After 15 minutes, hydrolysis of the TEOS led to the formation of a gel mass containing salts of cobalt and ruthenium.

The gel obtained was separated from the mother liquors, oven dried between 40° C. and 120° C., then calcined in air at 600° C.

The catalyst precursor obtained was reduced at atmospheric pressure by a mixture of hydrogen and nitrogen containing 6% of hydrogen in nitrogen between ambient temperature and 240° C., then in pure hydrogen between 240° C. and 450° C.

A solution 3 was prepared which contained 1.13 g of isopropyl orthotitanate in 50 ml of isopropanol.

After cooling to ambient temperature in hydrogen, the catalyst precursor was added to solution 3 in an inert atmosphere, and the mixture was stirred until solution 3 had completely decolorized.

After evacuation of the hydrogen in an inert atmosphere and passivation by a mixture of 1% of oxygen in nitrogen, solution 3 was gradually re-exposed to air. The solid was filtered, oven dried at 120° C., then catalyst I obtained was charged into a unit.

EXAMPLE 2

(In Accordance with the Invention): Catalyst J

A solution 1 containing 130 g of ethyl orthosilicate (TEOS) dissolved in 50 ml of ethanol and a solution 2 containing 46.3 g of hexahydrated cobalt nitrate, 0.14 g of trihydrated copper nitrate and 32 g of concentrated nitric acid dissolved in 80 cm³ of water, were mixed with vigorous stirring at ambient temperature.

After 19 minutes, hydrolysis of the TEOS led to the formation of a gel mass containing salts of cobalt and copper.

The gel obtained was separated from the mother liquors, oven dried between 40° C. and 120° C., then calcined in air at 600° C.

The catalyst precursor obtained was reduced at atmospheric pressure by a mixture of hydrogen and nitrogen containing 6% of hydrogen in nitrogen between ambient temperature and 240° C., then in pure hydrogen between 240° C. and 450° C.

A solution 3 was prepared which contained 1.13 g of isopropyl orthotitanate in 50 ml of isopropanol.

After cooling to ambient temperature in hydrogen, the catalyst precursor was added to solution 3 in an inert atmosphere, and the mixture was stirred until solution 3 had completely decolorized.

After evacuation of the hydrogen in an inert atmosphere and passivation by a mixture of 1% of oxygen in nitrogen, solution 3 was gradually re-exposed to air. The solid was filtered, oven dried at 120° C., then catalyst J obtained was charged into a unit.

EXAMPLE 3

(In Accordance with the Invention): Catalyst K

A solution 1 containing 130 g of ethyl orthosilicate (TEOS) dissolved in 50 ml of ethanol and a solution 2 containing 27.8 g of hexahydrated cobalt nitrate, 0.04 g of ruthenium hexamine trichloride and 32 g of concentrated nitric acid dissolved in 80 cm³ of water, were mixed with vigorous stirring at ambient temperature.

After 19 minutes, hydrolysis of the TEOS led to the formation of a gel mass containing salts of cobalt and ruthenium.

The gel obtained was separated from the mother liquors, oven dried between 40° C. and 120° C., then calcined in air at 600° C.

The catalyst precursor obtained was reduced at atmospheric pressure by a mixture of hydrogen and nitrogen containing 6% of hydrogen in nitrogen between ambient temperature and 240° C., then in pure hydrogen between 240° C. and 450° C.

A solution 3 was prepared which contained 0.11 g of isopropyl orthotitanate in 50 ml of isopropanol, in an inert atmosphere.

After cooling to ambient temperature in hydrogen, the catalyst precursor was added to solution 3 in an inert atmosphere, and the mixture was stirred until solution 3 had completely decolorized.

After evacuation of the hydrogen in an inert atmosphere and passivation by a mixture of 1% of oxygen in nitrogen, solution 3 was gradually re-exposed to air. The solid was filtered, oven dried at 120° C., then catalyst K obtained was charged into a unit.

EXAMPLE 4

(Comparative): Catalyst L

A solution 1 containing 130 g of ethyl orthosilicate (TEOS) dissolved in 50 ml of ethanol and a solution 2 containing 46.3 g of hexahydrated cobalt nitrate, 0.21 g of ruthenium hexamine trichloride and 32 g of concentrated nitric acid dissolved in 80 cm³ of water, were mixed with vigorous stirring at ambient temperature.

After 17 minutes, hydrolysis of the TEOS led to the formation of a gel mass containing salts of cobalt and ruthenium.

The gel obtained was separated from the mother liquors, oven dried between 40° C. and 120° C., then calcined in air at 600° C. Catalyst L obtained was charged into a unit.

EXAMPLE 5

(Comparative): Catalyst M

A solution 1 containing 130 g of ethyl orthosilicate (TEOS) and 1.13 g of isopropyl orthotitanate dissolved in 50 ml of ethanol and a solution 2 containing 46.3 g of hexahydrated cobalt nitrate, 0.21 g of ruthenium hexamine trichloride and 32 g of concentrated nitric acid dissolved in 80 cm³ of water, were mixed with vigorous stirring at ambient temperature.

After 15 minutes, hydrolysis led to the formation of a silica gel containing salts of cobalt, ruthenium and a hydrolysed titanium compound.

Catalyst M obtained was charged into a unit.

EXAMPLE 6

(Comparative): Catalyst N

The same gel as described in Example 1 was prepared, dried then calcined, but it was not reduced.

A solution 3 was then prepared which contained 1.13 g of isopropyl orthotitanate in 20 ml of isopropanol. The solid was then vacuum evaporated at 80° C., oven dried between 40° C. and 120° C. then calcined in air. Catalyst N obtained was charged into a unit.

TABLE 1

| | COMPOSITION OF CATALYSTS* | | | |
|---|---|---|---|---|
| EXAMPLE | CATALYST | Co | A | Ti |
| 1 | I (inv) | 25 | Ru:0.19 | 0.5 |
| 2 | J (inv) | 25 | Cu:0.10 | 0.5 |
| 3 | K (inv) | 15 | Ru:0.11 | 0.3 |
| 4 | L (comp) | 25 | Ru:0.19 | 0 |
| 5 | M (comp) | 25 | Ru:0.19 | 0.5 |
| 6 | N (comp) | 25 | Ru:0.19 | 0.5 |

*expressed as weight % of each element with respect to weight of silica

EXAMPLE 7

Catalytic Tests

Catalysts I, J, K, L, M and N prepared as described above in Examples 1 to 6 were tested in a fixed bed with a gas phase in a unit operating continuously using 20 cm³ of catalyst.

Catalysts I to N were first pre-reduced in-situ up to 240° C. by a mixture of hydrogen and nitrogen containing 6% of hydrogen in nitrogen, then in pure hydrogen up to 450° C., at atmospheric pressure. The test conditions were as follows:

Temperature 240° C.;
Pressure 2 MPa;
Hourly space velocity (HSV): 2000 h⁻¹;

$H_2/CO$ molar ratio: 2:1

TABLE 2

| CONVERSION OF SYNTHESIS GAS TO HYDROCARBONS | | | | | |
|---|---|---|---|---|---|
| | CO CONV (vol %) | DISTRIBUTION OF HYDROCARBONS FORMED (wt %) | | | CONVERSION VARIATION *Δ conv |
| CATALYST | after 100 h | $C_1$ | $C_2-C_4$ | $C_5^+$ | CO/1000 h (%) |
| I | 60 | 5.7 | 2.5 | 91.8 | +9 |
| J | 65 | 6.3 | 3.4 | 90.3 | −8 |
| K | 55 | 23.2 | 26.2 | 50 | −5 |
| L | 45 | 7.5 | 3.6 | 89.9 | −30 |
| M | 50 | 8.5 | 4.2 | 87.3 | −25 |
| N | 45 | 7.2 | 3.1 | 89.7 | −17 |

*= Conv CO/1000 h (%) − conv. CO (initial) (%)

We claim:

1. A process for the synthesis of essentially linear and saturated hydrocarbons containing at least 25% by weight of $C_5^+$ hydrocarbons with respect to the total amount of hydrocarbons formed, from a synthesis gas CO—($CO_2$)—$H_2$, in the presence of a catalyst, in which the synthesis gas is converted to hydrocarbons at a total pressure which is in the range 0.1 to 15 MPa, a temperature which is in the range 150° C. to 350° C., an hourly space velocity which is in the range 100 to 20000 volumes of synthesis gas per volume of catalyst per hour, and an $H_2/CO$ molar ratio in the synthesis gas in the range 1:2 to 5:1, said catalyst comprising (a) a support formed of at least one oxide of an element selected from the group consisting of: Si, Al, Ti, Zr, Sn, Zn, Mg or Ln (wherein Ln is a rare earth); (b) cobalt; (c) titanium; and (d) at least one additional element A selected from the group consisting of copper, ruthenium, platinum, palladium, scandium and yttrium, said catalyst having been produced by at least the following successive steps:

(1) forming a precursor comprising cobalt, element A and the support;

(2) at least partial reduction of said precursor in the presence of at least one reducing compound; and (3) depositing titanium on the reduced precursor.

2. A process according to claim 1, in which the catalyst comprises, as a % by weight of the support, between 1% and 60% of cobalt, between 0.01% and 20% of additional element A and between 0.01% and 15% of titanium.

3. A process according to claim 2, wherein element A is copper or ruthenium.

4. A process according to claim 1, in which the reduction of step (2) is substantially complete.

5. A process according to claim 1, in which the catalyst is pre-reduced before use, said catalyst pre-reduction being carried out by at least one reducing compound, optionally brought into contact with an inert gas in a reducing compound/(reducing compound+inert gas) molar ratio in the range 0.001:1 to 1:1, pre-reduction being carried out between 150° C. and 600° C., between 0.1 MPa and 10 MPa and at an hourly space velocity of 100 to 40000 volumes of mixture per volume of catalyst per hour.

6. A process according to claim 5, wherein the pre-reduction is conducted at a temperature of between 200° C. and 500° C.

7. A process according to claim 6, wherein element A is copper or ruthenium.

8. A process according to claim 5, wherein element A is copper or ruthenium.

9. A process according to claim 1, wherein element A is copper or ruthenium.

* * * * *